United States Patent [19]

Cannell et al.

[11] Patent Number: 6,015,574
[45] Date of Patent: *Jan. 18, 2000

[54] LIPOPHILIC CARRIER SYSTEMS

[75] Inventors: David W. Cannell, New York, N.Y.;
Hitren Mathur, Woodbridge, N.J.;
Nghi Nguyen, Edison, N.J.; Cynthia Espino, Princeton, N.J.

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/871,524

[22] Filed: Jun. 9, 1997

[51] Int. Cl.$^7$ ........................................................ A61R 9/10
[52] U.S. Cl. ............................................. 424/450; 516/145
[58] Field of Search .............................. 424/450; 516/145

[56] References Cited

U.S. PATENT DOCUMENTS

| 4,174,296 | 11/1979 | Kass | 252/312 |
|---|---|---|---|
| 4,874,553 | 10/1989 | Hager et al. | 260/403 |
| 5,002,761 | 3/1991 | Mueller et al. | |
| 5,173,303 | 12/1992 | Lau et al. | 424/450 |

FOREIGN PATENT DOCUMENTS

| 895719 A1 | 7/1983 | Belgium . |
|---|---|---|
| 123 071 | 10/1984 | European Pat. Off. . |
| 340 592 | 11/1989 | European Pat. Off. . |
| 521799 A1 | 1/1993 | European Pat. Off. . |

OTHER PUBLICATIONS

Ribosa, et al., International Journal of Cosmetic Science, "Physico–chemical Modifications of Liposome Structures Through Interaction With Surfactants," 1992: pp. 131–149.

*Primary Examiner*—James H. Reamer
*Attorney, Agent, or Firm*—Finnegan, Henderson, Farabow, Garrett & Dunner, L.L.P.

[57] ABSTRACT

A composition containing an organic phospholipid capable of forming bilayers in solution, a nonionic surfactant, and an amphoteric surfactant in a combined amount sufficient to allow lipophilic ingredients to be incorporated into an aqueous solution, and method for making such compositions.

22 Claims, No Drawings

LIPOPHILIC CARRIER SYSTEMS

FIELD OF THE INVENTION

The present invention relates to novel lipophilic carrier systems based on organic phospholipids capable of forming bilayers in aqueous solution, nonionic surfactants, and amphoteric surfactants.

BACKGROUND OF THE INVENTION

Organic phospholipids play an important role in the cosmetics and pharmaceutical industries because of their outstanding physiological properties, such as, for example, emulsifying, softening, and anti-oxidant effects. When hydrolyzed, organic phospholipids yield phosphoric acid, an alcohol, a fatty acid, and a nitrogenous base. Most phospholipids are amphipathic, i.e., have polar "heads" and non-polar "tails." As a result, most phospholipids tend to arrange spontaneously into a bilayer when suspended in an aqueous environment, with the polar heads contacting the water and the non-polar tails contacting each other. Most naturally occurring phospholipids prefer to form vesicular bilayers in water solutions. In such a bilayer vesicle, no non-polar part of the phospholipid has any contact with the water solution.

Because of their non-polar portions, phospholipids typically are water-insoluble and incompatible with many water soluble anionic compounds, such as anionic surfactants. While they can be solubilized in water at low levels by a range of surfactants, this is often not easily accomplished.

Instead, solubilization has been accomplished conventionally using specific solubilizing agents in aqueous alcoholic solutions. For example, U.S. Pat. No. 4,874,553 to Hager et al. discusses methods of rendering phospholipid mixtures water-soluble or water-dispersible by using certain amine compounds as solubilizing agents. U.S. Pat. No. 4,174,296 to Kass describes a method of improving the solubility of phospholipid compounds in water, in particular lecithin compounds, by mixing lecithin with specific single solubilizing agents, including amphoteric and anionic surfactants. These methods require alcohol for cosolubilization. Alcohol solutions have the drawback of disrupting any bilayer formation by altering the solution such that the alcohol functions as a secondary solvent.

Lecithins and other phospholipids have been used in the pharmaceutical industry to formulate carriers for water-insoluble drugs. For instance, in U.S. Pat. No. 5,173,303 to Lau et al., water-insoluble material is encapsulated by vesicles composed of phospholipids such as lecithin. I. Ribosa et al., in "Physico-chemical modifications of liposome structures through interaction with surfactants," Int'l Journal of Cosmetic Science 14: 131–149 (1992), also discuss solubilization of phospholipids via the interaction of liposomes with surfactants. Lau and Ribosa, however, investigated only dilute solutions of pure liposomes.

Despite difficulties in solubilization, certain organic phospholipids, such as lecithin, can advantageously give hair and skin a soft, moisturized feel because they have a strong affinity for the hydrophobic surface of the hair and skin. In addition, these phospholipids are toxicologically safe. It would thus be desirable for cosmetic and pharmaceutical applications to provide delivery systems that include such organic phospholipids as a carrier for other lipophilic ingredients, without the need for alcohols and other similar solvents.

SUMMARY OF THE INVENTION

In order to achieve these and other advantages, the present invention is drawn to a composition made up of at least one organic phospholipid capable of forming bilayers in aqueous solution, at least one nonionic surfactant, and at least one amphoteric surfactant. The nonionic surfactant is present in an amount equal to or greater than the amount of the organic phospholipid.

In another embodiment, the present invention relates to an aqueous delivery system for lipophilic materials. The delivery (or "carrier") system includes at least one organic phospholipid capable of forming bilayers in aqueous solution, at least one nonionic surfactant, at least one amphoteric surfactant, at least one lipophilic ingredient, and an aqueous phase. The nonionic surfactant is present in an amount by weight equal to or greater than the amount of the phospholipid. The organic phospholipid, the nonionic surfactant, and the amphoteric surfactant are present in a combined amount sufficient to allow the lipophilic ingredient to be incorporated into the delivery system.

The present invention is also drawn to a process for the preparation of an aqueous system comprising: (a) combining at least one organic phospholipid capable of forming bilayers in aqueous solution, at least one nonionic surfactant, and at least one amphoteric surfactant to form a mixture, (b) heating the mixture obtained in step (a), (c) adding an aqueous solution to form a diluted mixture, and (d) cooling the diluted mixture. Lipophilic ingredients can be incorporated in step (a).

Reference will now be made in detail to the present preferred embodiment(s) of the invention.

DETAILED DESCRIPTION OF THE PREFERRED EMBODIMENTS

Advantageously, the present invention allows oil-soluble (lipophilic) materials or ingredients to be solubilized in an aqueous solution with no oily feel. No alcohol is required for cosolubilization, and there is no need for liposome preparation. Further, when the water evaporates, the residue left behind includes the oil-based material and/or the phospholipid. These materials will, for example, moisturize or condition the skin and/or the hair.

The composition of the invention is also easy to formulate and is gentle on the hair or skin because of the mild surfactants used. Unlike the attempted solubilization of phospholipids in the prior art, the present invention requires the presence of at least one nonionic surfactant and at least one amphoteric surfactant in the concentrated solutions of lecithin.

The compositions and delivery systems of the present invention readily deposit the organic phospholipid/lipophilic substances on the hair and skin and, because of their inherent insolubility, resist being washed off with water. Accordingly, these compositions and delivery systems can be used in hair shampoos, conditioners, hair dyeing compositions, including oxidative dyes, permanent waves, relaxers, bath and body products, sunscreens, or cosmetics.

These systems could also be used to deliver active lipophilic pharmaceutical ingredients, particularly in topical applications. Such systems could further help protect against oxidation and rancidity by protecting sensitive ingredients in pharmaceuticals or foods.

Additionally, the "lipophilic load" carried by these systems can be quite high, a benefit that inures both to the user and to the manufacturer in an economic sense. Load is defined as the weight of added hydrophobe or lipophile divided by the weight of the phospholipid expressed as a percentage. Thus, 1 g of lipophile in a composition with 5 g phospholipid is a ⅕ or 20% load. 50% is considered a high lipophilic load and can be achieved with certain lipophiles and surfactant combinations.

Without being bound to a particular theory, the inventors believe that in the composition of the present invention, an organized structure, likely a laminar gel, is formed between the organic phospholipid and the nonionic surfactant and is solubilized by the amphoteric surfactant. The organized structure can incorporate other lipophiles. In aqueous systems, the structure remains organized, as evidenced by the clarity of the solution, exhibiting a slight Tyndall light scattering effect, and, when concentrated, showing lamellar anisotropic structures under polarized light.

In one embodiment, therefore, the invention is drawn to a composition comprising at least one organic phospholipid capable of forming bilayers in aqueous solution, at least one nonionic surfactant, and at least one amphoteric surfactant, where the nonionic surfactant is present in an amount by weight equal to or greater than the amount of the phospholipid. Neither the amphoteric nor the nonionic surfactant alone will give a satisfactory solution with the organic phospholipids. When dissolved in either an amphoteric or a nonionic surfactant, solubility for the lecithin was poor compared to the mixture of surfactants of the present invention.

With respect to the ingredients of the inventive composition, the preferred organic phospholipids capable of forming bilayers in aqueous solution are lecithins. Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, Alcolec S is a fluid soy lecithin, Alcolec F 100 is a powder soy lecithin, and Alcolec Z3 is a hydroxylated lecithin, all of which are available from the American Lecithin Company.

In the present invention, lecithin is preferably used in an amount greater than 0 to about 5% by weight of the composition as a whole. Since lecithin itself is not a pure raw material and may have free glycerides, glycerin, fatty acids, and soaps, adjustments in this ratio may need to be made, i.e., one source of lecithin may require different ratios of nonionic and amphoteric surfactants than another to achieve maximum clarity of solution. Preferably, the composition of the invention forms a clear solution, though the purpose of the invention is achieved just as effectively with a slightly cloudy solution.

Other than lecithins, another group of phospholipids which may be useful in the present invention are multifunctional biomimetic phospholipids. For example, the following multifunctional biomimetic phospholipids manufactured by Mona Industries may be useful: PHOSPHOLIPID PTC, PHOSPHOLIPID CDM, PHOSPHOLIPID SV, PHOSPHOLIPID GLA, and PHOSPHOLIPID EFA.

The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain, more preferably a $C_{16}$ to $C_{18}$ carbon chain, derivatized to yield a Hydrophilic-Lipophilic Balance (HLB) of at least 10. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 10. Preferably the nonionic surfactants contain ethoxylate in a molar content of from 10–25, more preferably from 10–20 moles.

Nonionic surfactants may be selected from, but are not limited to, the following:

| # of Cs | Name | Trade Name |
|---|---|---|
| C-12 | Laureth-23 | BRIJ 35, available from ICI Surfactants |
| C-16 | Ceteth-10 | BRIJ 56, available from ICI Surfactants |
| C-16 | Ceteth-20 | BRIJ 58, available from ICI Surfactants |
| C-16 | IsoCeteth-20 | Arlasolve 200, available from ICI Surfactants |
| C-18 | Steareth-10 | Volpo S-10, available from Croda Chemicals Ltd. |
| C-18 | Steareth-16 | Solulan-16, available from Amerchol Corp. |
| C-18 | Steareth-20 | BRIJ 78, available from ICI Surfactants |
| C-18 | Steareth-25 | Solulan-25, available from Amerchol Corp. |
| C-18 = | Oleth-10 | BRIJ 97, available from ICI Surfactants |
| C-18 = | Oleth-20 | Volpo-20, available from Croda Chemicals Ltd. |

Alkyl polyglucose surfactants sold under the name PLANTAREN, available from Henkel, may also be used. The nonionic surfactant is preferably present in an amount of about 5 to 20% by weight relative to the weight of the whole composition when 5 % lecithin is used. More preferably, the nonionic surfactant is present in an amount of about 10 to 20% by weight.

The amphoteric surfactants useful in the present invention include, but are not limited to, betaines, sultaines, hydroxysultaines, alkyl amphodiacetates, alkyl amphodipropionates, and imidazolines, or salts thereof. It is recognized that other fatty acid condensates such as those formed with amino acids, proteins, and the like are suitable. Cocamphodipropionate is particularly preferred, for example, Miranol C2M-SF (disodium cocamphodipropionate), in its salt-free form, available from Rhone-Poulenc. Also preferred is Crosultaine C-50 (cocamidopropyl hydroxysultaine), available from Croda The amphoteric surfactants are preferably present in the composition in an amount ranging from about 5 to 20% by weight of the composition as a whole when 5% of the organic phospholipid, preferably lecithin, is used, more preferably from about 10 to 20% by weight.

In one embodiment of the composition of the present invention, the organic phospholipid capable of forming bilayers in aqueous solution, amphoteric surfactant, and nonionic surfactant are present in a ratio ranging from about 5:10:10 (1:2:2) to about 5:20:20 (1:4:4) by weight relative to the whole composition. Preferably the ratio is 1:3:3, and still more preferably 1:3:2. The loading capability for lipophiles carried by the delivery system of the present invention is maximized if the ratio of nonionic surfactant to phospholipid is minimized, with the bilayers still being solubilized, because an excess of nonionic surfactant may disrupt the organized structure.

In a particularly preferred embodiment, the composition of the present invention comprises Alcolec S (soy lecithin), Miranol C2M-SF (disodium cocamphodipropionate, an amphoteric surfactant) and Arlasolve 200 (IsoCeteth-20, a nonionic surfactant) in a ratio of 5:15:10 (1:3:2) by weight relative to the whole composition. In general, the preferred compositions of the invention are known as the "LAN" because they contain a lecithin (L), an amphoteric surfactant (A), and a nonionic surfactant (N). Although lecithin is particularly preferred, the amphoteric and nonionic surfactants may vary.

When used as an ingredient in further formulations, the LAN is compatible and generally gives clear solutions with anionic surfactants such as alkyl sulfates and ethoxylated alkyl sulfates. Other anionic surfactants such as sulfosuccinates may also be used. Typically, LAN compositions can resist storage at 45° C. for three months or more, which would predict that they have a shelf life at room temperature of at least three years.

In another aspect, the present invention relates to a an aqueous delivery or carrier system comprising: at least one organic phospholipid capable of forming bilayers in aqueous solution, at least one nonionic surfactant present in an amount greater than or equal to the amount of the phospholipid, at least one amphoteric surfactant, at least one lipophilic ingredient, and an aqueous phase. The lecithin, nonionic surfactant, and amphoteric surfactant are present in a combined amount sufficient to allow the at least one lipophilic ingredient to be incorporated into the aqueous system.

Lipophilic "ingredients" or "materials" suitable for use in the system of the invention include but are not limited to: silicones, oil-soluble vitamins such as Vitamin E and Vitamin A, ceramides and natural oils. The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octanediol, octylmethoxy cinnamate, octyl salicylate, and silicones such as dimethicone, cyclomethicone, phenyl trimethicone, and laurylmethicone copolyol.

The aqueous phase can contain additional ingredients such as anionic surfactants, inorganic salts, proteins, hair dyes, water-soluble polymers, quaternary ammonium compounds, complex and simple carbohydrates, amino acids, preservatives and fragrances.

If the inventive system is to be used in concentrated form, i.e., with about 5% by weight of the organic phospholipid and 1% of added lipophile, the composition preferably has a pH ranging from 4–12 for maximum stability and clarity. The more concentrated the solution, the better the delivery.

If this blend is diluted with water or the blend is used as an ingredient in another composition, then the pH has a broader range, i.e., preferably ranges from 2–12, and a wider variety of additives can be included in the solution. When water is added to a concentrated LAN, it may appear to form a cloudy solution at first if a large amount of water is added at once. The LAN will eventually go into solution, however, and become clear or at least clearer. The time to clear decreases as the LAN ratio increases. Once the organized structure of the LAN forms, the addition of more water does not affect clarity. These dilute blends are still very effective in delivering lipophilic ingredients. The blends can be freeze-dried to gums that redissolve into water.

A process for preparing the aqueous system of the present invention comprises: (a) combining the following ingredients to obtain a mixture: at least one organic phospholipid capable of forming bilayers in aqueous solution, at least one nonionic surfactant, and at least one amphoteric surfactant, where the nonionic surfactant is present in an amount by weight equal to or greater than the amount of the organic phospholipid, (b) heating the mixture obtained in step (a), and (c) adding an aqueous solution to the heated mixture to obtain the desired carrier system. Lipophilic ingredients may be added in step (a). Preferably the carrier system obtained can carry a high load (i.e., 50% is considered a high load) of the organic phospholipid/lipophilic ingredient. The mixture is preferably heated at a temperature of 65° C. to 85° C., depending on the melting points of the solid surfactants.

More specifically, the preparation of the carrier system of the present invention may be carried out as follows. Lecithin (L) is dispersed in water. The lipophile is combined with nonionic surfactant(s) (N) at appropriate ratios and added to the lecithin/water dispersion. An amphoteric surfactant (A) is added and the mixture is heated, preferably to a temperature of from 75° C. to 85° C. The combination of these ingredients results in a solution which is clear to slightly hazy and is referred to as the "LAN," which can then be used as a "raw material" to make finished products.

Alternatively, lecithin, amphoteric surfactant(s) and nonionic surfactant(s) can be weighed to appropriate ratios and heated to 70° C. with stirring. Water is then added q.s. at the same temperature. Another alternative method of preparation comprises adding the lipophile with mixing after solutions have cooled. This last alternative method helps protect heat-sensitive lipophiles.

The resulting compositions may vary from clear to slightly hazy and are infinitely dilutable with water. The slight haze can be overcome by adjusting the ratio of lecithin to the surfactants, adjusting pH, or reducing lipophile concentrations.

The composition and carrier system of the present invention can be used as an ingredient itself in, for example, shampoos, conditioners (rinse-off and leave-in), deep treatments for hair, body washes, bath gels, hair dyeing compositions, permanent wave formulations, relaxers, make-up preparations, skin creams or lotions.

The carrier system of the present invention can be used to formulate hair products for color-treated hair, dry hair, fine hair, and damaged hair. For each type of hair, the LAN can be used to create a regimen comprising shampoo, conditioner, and deep treatment, (i.e., deep conditioner). LAN compositions used for these products preferably contain lecithin (L), at least one amphoteric surfactant (A), such as disodium cocoamphodipropionate, and at least one nonionic surfactant (N), e.g., a blend of Oleth-10 and PPG-5-Ceteth-20. Additional nonionic, amphoteric, and also anionic surfactants can be added. The LAN compositions may further contain at least one lipophile (also referred to as a hydrophobe) such as the following:

(1) For dry brittle hair, olive oil can be used. Mineral oil or other emollient oils can also be used.

(2) To protect color-treated hair from exposure to the sun and other environmental elements, octyl salicylate, Vitamin E (Tocopherol) and octyl methoxycinnamate are suitable.

(3) In products for chemically treated hair and fine hair, the ceramide 2-Oleamido-1,3-octadecanediol is useful. Other ceramides could also be used.

In general, the concentration of the LAN is increased within each regimen from shampoo to conditioner to deep treatment. Thus, the deep treatment formulations have the most concentrated lipophile-carrying LAN.

The LAN systems of the invention can be further associated, in the products described above, with proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the hair. Cationic proteins or proteins in general may be stabilizers for the LAN and enhance its delivery by changing the charge on the surface of the LAN structure. The skin and the hair attract cationic ingredients, and proteins are generally substantive to these tissues.

In conditioning emulsions, nonionic emulsifiers such as glyceryl stearate and PEG-100 stearate can be used, and the LAN is treated as a lipophilic ingredient itself.

Other ingredients in the LAN compositions may include cationic polymers, such as polyacrylamide, and polyquaternium 10 and 11, cationic conditioners, such as quaternium 27, behenamidopropyl PG-dimonium chloride, hydroxyethyl tallowdimonium chloride, hexadimethrine chloride, stearalkonium chloride, and cetrimonium chloride, isoparaffins, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

Further, shampoos, conditioners, and deep treatments within the scope of the present invention may be used on hair which has been treated, e.g., with color (dye or bleach) or chemicals (permanent wave or straightening), or which is dry or fine and show significant substantivity for the hair.

Two parameters give a quantitative measure of how difficult (or easy) it is to comb a swatch of hair. "Combing work" is the total energy needed to comb through the whole hair swatch. "Average load" is the average force for the comb to travel through the swatch. Combing work and average load are consistently significantly lower for hair treated with a product of the invention. Even hair that is treated with the invention and then exposed to irradiation and other environmental elements shows much better results than untreated hair. In all cases, hair treated with the compositions of the present invention is much easier to comb, wet or dry, than untreated hair.

The invention will be further clarified by the following examples, which are intended to be illustrative of the invention, but not limiting thereof.

EXAMPLES

Example 1

Determining Solubility Parameters in Mixture of Surfactants 5 g lecithin was dissolved in mixtures of Miranol C2M-SF (amphoteric surfactant) and Arlasolve 200 (Iso-Ceteth-20, nonionic surfactant). The lipophilic ingredient was olive oil. The results are shown in Tables 1 and 2 below.

TABLE 1

Optimizing Ratios of LAN Containing Olive Oil

| | Olive Oil/Lecithin Ratio (LOAD) | | | | | |
|---|---|---|---|---|---|---|
| | 0.2 | 0.3 | 0.4 | 0.5 | 0.6 | 1 |
| 1:3:2 LAN | clear | hazy | cloudy | cloudy | cloudy | cloudy |
| 1:3:3 LAN | clear | cloudy | cloudy | cloudy | cloudy | cloudy |
| 1:4:4 LAN | clear | clear | clear | clear | clear | cloudy |
| 1:5:5 LAN | clear | clear | clear | clear | clear | cloudy |

In Table 1, lecithin was fixed at 5 g, and various ratios of the LAN were studied as a function of load from 20 to 100%. (Load equals weight of added lipophile divided by weight of lecithin). At the lowest ratios of surfactants to lecithin increases, however, the organized structure broke down. Thus, even though the LANs with bigger ratios of surfactants to lecithin theoretically can carry more lipophile, optimum results are achieved with a maximum of lecithin to a minimum of surfactant. The results show that a ratio of 1:3:2 gave a clear, dilutable mixture with olive oil.

TABLE 2

Optimizing the Amount of Nonionic and Amphoteric Surfactants

| LECITHIN | AMPHOTERIC | NONIONIC | CLARITY | RATIO |
|---|---|---|---|---|
| 5 g | 10 g | 10 g | cloudy | 1:2:2 |
| 5 g | 10 g | 8 g | cloudy | 1:2:1.6 |
| 5 g | 15 g | 15 g | clear | 1:3:3 |
| 5 g | 15 g | 10 g | clear | 1:3:2 * |
| 5 g | 15 g | 5 g | cloudy | 1:3:1 |
| 5 g | 15 g | 3 g | cloudy | 1:3:0.6 |
| 5 g | 15 g | 8 g | cloudy | 1:3:1.6 |
| 5 g | 12 g | 10 g | cloudy | 1:2.4:2 |
| 5 g | 12 g | 8 g | cloudy | 1:2.4:1.6 |
| 5 g | 13 g | 9 g | cloudy | 1:2.6:1.8 |

* optimum ratio

Table 2 does not consider lipophilic load. The amounts of amphoteric and nonionic surfactants thus varied over a wider range of concentrations around the pair of points that are clear at 20% load in Table 1 (1:3:2) and (1:3:3). The table shows that the LAN ratio made a difference in the clarity of the solution. When the amount of the nonionic surfactant was increased, the solutions remained clear, but when the amount was decreased, the solutions became cloudy. The ratio of amphoteric to nonionic surfactant is maintained at a certain level for optimum results to be obtained but the total concentration of surfactants plays a role as well. For instance, when the ratio of amphoteric surfactant to nonionic surfactant was maintained at 3:2 and the total surfactant concentration was decreased relative to lecithin (i.e., from 1:3:2 to 1:2.4:1.6, which is the same ratio but different relative concentrations), the result was a cloudy solution. In this case, increasing the nonionic to 2.0, for example, did not clarify the mixture at this weight of lecithin.

The dilutability of solutions above the ratio of 1:2:2 (5:10:10) was infinite, though at that ratio the solutions were not quite clear. At a LAN ratio of 1:3:2, the solution was generally both clear and infinitely dilutable.

Example 3

Study of Solubility of Lipophilic Ingredients

The solubility of 2-oleamido-1,3-octanediol (a ceramide) and olive oil, lipophilic ingredients often used in hair care products, was evaluated in a mixture comprising 5 g lecithin and varying amounts of Miranol C2M-SF and Arlasolve 200. Both 2-oleamido-1,3-octanediol and olive oil, at the 1% level, formed a clear, stable lecithin solution with 15% (15 g) Miranol and 10% (10 g). Thus, the lipophiles were solubilized best with a LAN ratio of 1:3:2.

Example 4

Study of HLB Values

Using different ratios of the nonionic surfactants BRIJ 72 (HLB 4.9) and BRIJ 700 (HLB 18.8), an HLB range from 5 to 18 was obtained. Only the even HLB values were studied. The formulations tested contained 5% Alcolec S, 15% Miranol C2M-SF conc, and 15% nonionics (ratio 1:3:3) with different HLB's. Surprisingly, none of the HLB values investigated provided clear solutions. In each case, thick gels were formed instead of solutions. See Table 3. This experiment showed that it is preferable to use a mixture of nonionic surfactants with similar HLB's, since the blends of large and small HLB's gave only very cloudy solutions.

TABLE 3

HLB Systems (q.s. to 100 g water)

| LECITHIN | AMPHOTERIC SURFACTANT | NONIONIC SURFACTANT | OTHER INGRED | CLARITY | STABILITY |
|---|---|---|---|---|---|
| 5 g | 15 g | 13.82 g BRIJ 72 + 1.18 g BRIJ 700 (HLB 6) | — | very cloudy | — |
| 5 g | 15 g | 11.66 g BRIJ 72 + 3.34 g BRIJ 700 (HLB 8) | — | very cloudy | — |
| 5 g | 15 g | 9.5 g BRIJ 72 + 5.5 g BRIJ 700 (HLB 10) | — | very cloudy | — |
| 5 g | 15 g | 7.34 g BRIJ 72 + 7.66 g BRIJ 700 (HLB 12) | — | very cloudy | — |
| 5 g | 15 g | 5.18 g BRIJ 72 + 9.82 g BRIJ 700 (HLB 14) | — | very cloudy | — |
| 5 g | 15 g | 3.02 g BRIJ 72 + 11.98 g BRIJ 700 (HLB 16) | — | very cloudy | — |
| 5 g | 15 g | 0.86 g BRIJ 72 + 14.14 g BRIJ 700 (HLB 18) | — | very cloudy | — |

\* BRIJ 72 = Steareth-2 HLB 4.9
\* BRIJ 700 = Steareth-100 HLB 18.8

Example 5
Study of Solubility and Effectiveness of Dyes in the LAN

Solubility and effectiveness of dyes used in combination with the LAN were studied. The LAN provides three novel and surprising aspects to hair coloring/dyeing preparations in particular: (1) The LAN obviates the need for classical cosolvents typically included in hair coloring compositions such as ethanol, alkyl polyols, or propylene glycol, which serve to help solubilize dyestuffs into the color base; (2) No quaternized amine compounds are needed to effect conditioning of the hair when the LAN is used; and (3) No nitrogen blanketing of the hair color composition is necessary during the compounding or storage of these compositions.

| Dye Composition 1 | | |
|---|---|---|
| Deionized water | 61.4 g | |
| Sodium sulfite | 1.0 g | [antioxidant] |
| Isoascorbic acid | 0.8 g | [antioxidant] |
| para-phenylenediamine | 0.8 g | |
| p-amino-ortho-cresol | 0.15 g | |
| meta-aminophenol | 0.3 g | |
| para-aminophenol | 0.5 g | |
| 2,4-diaminophenoxyethanol | 0.05 g | |

The deionized water at 70° C. was added to a glass beaker, followed by the rest of the above ingredients. In another beaker, 5 g soy lecithin, 15 g disodium cocamphodipropionate, and 15 g isoceteth-20 (the LAN, in a ratio of 1:3:3) were heated to 70° C. and added to the aqueous phase with stirring. The pH was adjusted by adding aliquots of ammonium hydroxide to a pH of 8.4.

The resulting clear, pale amber hair color composition was stored for 5 weeks in a glass bottle. No nitrogen blanket was used. No crystallization occurred. No darkening of the solution occurred either.

A 10 g portion of the hair color composition was added to a plastic bowl and mixed with an equal volume of 20 vol hydrogen peroxide and then applied to level 6 natural brown hair, also containing 25% grey hair, for 20 minutes at ambient temperature. After 20 minutes, the hair was rinsed under running tap water for 10 minutes, dried with a commercial hair dryer to give L=19.11, a=0.82, b=−0.03.

L, a, and b are defined as follows. L indicates the lightness or darkness of the color value. The higher the L, therefore, the lighter the hair, and the more fading that has occurred. When L is 0, the hair is black, and when L is 100, the hair is white. −a and +a represent changes in color tone from green to red. −b and +b represent the changes in color tone from blue to yellow. In the present example, the hair color overall decreased to a medium brown tone of level 4 depth.

Dye Composition 2

Dye Composition 1 was prepared except that the antioxidant was 1.8 g isoascorbic acid instead of isoascorbic acid plus sodium sulfite. The resulting clear, pale amber hair color composition was stored for 5 weeks in a glass bottle. No nitrogen blanket was used. No crystallization occurred. No darkening of the solution occurred. The composition was applied to the hair as above, with the following results: L=22.11, a=0.70, b=−0.07. The hair color overall decreased to a brown tone of level 5 depth.

Dye Composition 3

Dye composition 1 was prepared, except that the pH was adjusted to 10. The resulting clear, pale amber hair color composition was stored for 5 weeks in a glass bottle. No nitrogen blanket was used. No crystallization occurred. No darkening of the solution occurred. The composition was applied to hair as above, with the following results: L=21.32, a=2.60, b=1.51. The hair color overall decreased to a brown tone of level 5 depth with red/gold tones.

Dye Composition 4

Dye composition 2 was prepared except that the pH was adjusted to 10. The resulting clear, pale amber hair color composition was stored for 5 weeks in a glass bottle. No nitrogen blanket was used. No crystallization occurred. No darkening of the solution occurred. The composition was applied to hair as above, with the following results: L=21.66, a=2.77, b=1.46. The hair color overall decreased to a brown tone of level 5 depth with red/gold tones.

Dye Composition 5

In a beaker, 5 g soy lecithin, 15 g disodium cocamphodipropionate, and 15 g isoceteth-20 (the LAN, in a ratio of 1:3:3) were heated to 70° C. Next, 0.8 g para-phenylenediamine, 0.15 g p-amino-ortho-cresol, 0.3 g meta-aminophenol, 0.5 g para-aminophenol, and 0.05 g 2,4-diaminophenoxyethanol were added to the melted composition with stirring. The stirred mixture was then added with stirring to 61.4 g deionized water at 70° C. containing 1.8 g isoascorbic acid and 0.8 g sodium sulfite. The pH was adjusted by adding aliquots of ammonium hydroxide to a pH of 10.

To a 40 g portion of the above composition was added 4 g of steareth-10 allyl ether/acrylates copolymer. The resulting clear pale amber gel was stored in a glass bottle for 5 weeks. No nitrogen blanket was used. No crystallization occurred. No darkening of the solution occurred.

As in dye composition 1, a 10 g portion of the hair color composition was added to a plastic bowl and mixed with an equal volume of 20 vol hydrogen peroxide and then applied to level 6 natural brown hair, containing 25% grey hair, for 20 minutes at ambient temperature. After 20 minutes, the hair was rinsed under running tap water for 10 minutes, dried with a commercial hair dryer to give L=20.69, a=1.72, b=0.86. The hair color overall decreased to a brown tone of level 5 depth with red/gold tones.

Dye compositions 1–5, formulated with the LAN, left the hair soft and conditioned and were stable solutions, lasting 5 weeks in storage before being used, and lasting much longer after that. LAN compositions containing added lipophiles have been stored for over 3 months at 45° C., yielding a predicted shelf life of 3 years at room temperature. Such LAN-containing solutions obviate the need for added co-solvents in such compositions.

Example 6

Study of Solubility of Lipophilic Ingredients in LANs of varying pH

Concentrated LAN solutions containing various lipophilic ingredients were studied at pH values ranging from 3 to 12. The lecithin was present at 5%, and the lipophilic ingredient was present in an amount of 1%. The LAN itself and the LAN plus a lipophile were cloudy at pH 3–5. At pH 6, the LAN itself was clear. At pH 11 and 12, all the solutions were clear. See Table 5.

TABLE 5

PROPERTIES OF CONCENTRATED LAN SOLUTIONS
CONTAINING LIPOPHILIC INGREDIENTS
(1:3:3 LAN ratio, 5% lecithin, 1% lipophilic ingredients)

| Ingredient | pH 3 | pH 4 | pH 5 | pH 6 | pH 7 | pH 8 | pH 9 | pH 10 | pH 11 | pH 12 |
|---|---|---|---|---|---|---|---|---|---|---|
| LAN | • | • | • | ○ | ○ | ○ | ○ | ○ | ○ | ○ |
| +olive oil | • | • | • | • | ○ | ○ | ○ | ○ | ○ | ○ |
| +octyl methoxy cinnamate | • | • | • | • | • | • | • | ○ | ○ | ○ |
| +tocopherol | • | • | • | • | • | • | • | ○ | ○ | ○ |
| +octylcrylene | • | • | • | • | • | • | • | • | ○ | ○ |
| +Ceramide R | • | • | • | • | • | • | • | • | ○ | ○ |

(Shaded areas indicate non-adjusted pH)
• = CLOUDY
○ = CLEAR

The table shows that concentrated LAN solutions must be more alkaline to be clear. Thus, the solutions at pH 10–12 had the best results.

|  | Amount in wt % | |
|---|---|---|
| Ingredient | A | B |
| Silicone | 2.0 | 2.0 |
| Lecithin | 4.0 | 4.0 |
| PPG-5-Ceteth-20 | 14.0 | — |
| Oleth-10 | — | 15.0 |
| Decyl glucoside | 15.0 | 10.0 |
| Disodium cocoamphodipropionate | 19.0 | 1.0 |
| Water | q.s. | q.s. |
| pH adjusted to 6.0–6.5 with phosphoric acid | | |
| A: Load = 50%  LAN ratio = 1:4.75:7.25 | | |
| B: Load = 50%  LAN ratio = 1:0.25:6.25 | | |

These LAN/silicone combinations could then be used to easily incorporate the silicone into shampoos, conditioners, and other formulations.

Example 8

Preparation of a Clear Shampoo for Color-Treated Hair

The following clear shampoo was formulated. It contained a LAN carrying sunscreens and Vitamin E. All ingredient amounts are shown in weight percent.

The LAN* . . . 0.100% of the following LAN composition:

| | |
|---|---|
| lecithin . . . | 4.00% |
| disodium cocoamphodipropionate (amphoteric surfactant) . . . | 19.00% |
| PPG-5-Ceteth-20 (nonionic surfactant) . . . | 14.00% |
| Oleth-10 (nonionic surfactant) . . . | 9.00% |
| methyl paraben . . . | 0.20% |
| ethyl paraben . . . | 0.10% |
| disodium EDTA . . . | 0.10% |
| phenoxyethanol . . . | 0.50% |
| phosphoric acid 85% (pH adjuster) . . . | 1.40% |
| water . . . | 49.70% |
| Vitamin E (tocopherol) . . . | 1.00% |
| octyl salicylate (sunscreen) . . . | 1.00% |

* This LAN is carrying a 50% load: 2.00% total lipophiles (vitamin E and octyl salicylate) and 4.00% lecithin.

In a shampoo base of:

| | |
|---|---|
| sodium laureth sulfate (anionic surfactant) . . . | 25.000% |
| polyquaternium 10 (polymer) . . . | 0.100% |
| PPG-5-Ceteth-10-phosphate emollient . . . | 0.500% |
| disodium cocoamphodipropionate and cocamidopropyl betaine . . . (amphoteric surfactants) | 13.00% |
| octyl methoxy cinnamate (sunscreen) . . . | 0.100% |
| phosphoric acid (85%) . . . | 0.800% |
| hydrochloride lauryldimonium hydroxypropyl hydrolyzed soy . . . protein, and hydrolyzed soy protein with wheat amino acid | 0.400% |
| trehalose (humectant) . . . | 0.001% |
| water . . . | q.s. to 100 |

Example 7

Preparation of Silicone/LAN Combinations

Silicones are highly desirable ingredients to enhance shine and softness but are difficult to formulate because of their inherent insolubility in water and alcohol. The silicones, phenyl trimethicone (A) and laurylmethicone copolyol (B), were formulated into LAN serums to yield clear, dilutable solutions. The nonionic surfactants were PPG-5-Ceteth-20, Oleth-10, and also decyl glucoside. The amphoteric surfactant was disodium cocoamphodipropionate.

Example 10

Preparation of a Deep Treatment for Color-Treated Hair

The following viscous aqueous fluid containing cationic conditioners, silicones, cationic polymers (e.g., polyacrylamide), sunscreens and Vitamin E, was formulated:

| | |
|---|---|
| The LAN . . . same LAN formulation as set forth in example 8 . . . | 20.000% |

In a treatment base of:

| | |
|---|---|
| gums and resins selected from polyacrylamide, $C_{13}$–$C_{14}$ isoparaffin, laureth 7, and xanthan gum | 3.000% |
| behenamidopropyl PG-dimonium chloride (cationic conditioner) . . . | 3.000% |
| cetrimonium chloride (cationic conditioner) . . . | 3.000% |
| cyclomethicone and dimethicone . . . | 3.000% |
| octyl methoxycinnamate (sunscreen) . . . | 0.100% |
| propylene glycol fragrance . . . | 0.500% |
| preservatives selected from phenoxyethanol, methylparaben, ethylparaben, and disodium EDTA . . . | 0.800% |
| | 0.800% |
| proteins and amino acids selected from taurine, arginine hydrochloride, lauryldimonium hydroxypropyl hydrolyzed soy protein, and hydrolyzed soy protein with wheat amino acid | 1.210% |
| phosphoric acid 85% (pH adjuster) . . . | 0.060% |
| trehalose (humectant) . . . | 0.001% |
| water . . . | q.s. to 100 |
| sodium chloride . . . | 0.500% |
| fragrence . . . | 0.500% |
| preservatives selected from phenoxyethanol, methylparaben, ethylparaben, and disodium EDTA . . . | 0.800% |
| proteins and amino acids selected from taurine, arginine hydrochloride, lauryldimonium hydroxypropyl hydrolyzed soy protein, and hydrolyzed soy protein with wheat amino acid . . . | 0.400% |
| trehalose (humectant) . . . | 0.001% |
| water . . . | q.s. to 100 |

Example 9
Preparation of a Conditioner for Color-Treated Hair

The following emulsified cream treatment containing cationic conditioners, silicones, cationic polymers, sunscreens and Vitamin E, was formulated:

| | |
|---|---|
| The LAN . . . same LAN formulation as set forth in example 8 . . . | 0.500% |

In a conditioner base of:

| | |
|---|---|
| glyceryl stearate and PEG-100 stearate (nonionic emulsifiers) . . . | 5.000% |
| quaternium 27 . . . | 4.000% |
| hexadimethrine chloride and hydroxyethyl cellulose (cationic and cellulosic polymers) | 1.300% |
| octyl methoxycinnamate (sunscreen) . . . | 0.100% |
| dimethicone (silicone) . . . | 2.000% |
| stearyl alcohol (emollient) . . . | 5.000% |
| octyldodecanol (emollient) . . . | 2.000% |
| sodium citrate . . . | 0.150% |
| fragrance . . . | 0.500% |
| preservatives selected from phenoxyethanol, methylparaben, ethylparaben, propylparaben and disodium EDTA proteins and amino acids selected from taurine, arginine | 0.900% |

Example 11
Color Retention Effects of Color Treatment Products Against Chlorine Water and Shampooing Dyed brown hair was treated with 5 ppm chlorine water during a regime of deep treatment, shampoo and conditioner formulated as described above for color-treated hair for 1 week (1 deep treatment, 4 shampoos and 4 conditioners). To obtain significant experimental data, an experiment was carried out in which 72 brown hair swatches were colored, followed by:

24 swatches treated with: Treatment (10 minutes/room temperature (RT), rinse) Shampoo (5 minutes/RT, rinse) Conditioner (10 minutes/RT, rinse)

The shampoo and conditioner treatment was repeated 3 more times, representing one week of product use, and the chlorine treatments (5 ppm chlorine water for 30 minutes at room temperature/rinse) were done after the 1st and the 4th cycle:

24 swatches treated with chlorine water during the regimen for color-treated hair as described above but without Arginine, Taurine, Proteins, LAN, Vitamin E, sunscreens in the products 24 swatches treated with chlorine water during the regimen for color-treated hair as described above but with water instead of the described hair products The table below shows that frequent use of the products for color-treated hair protects the color from fadage against chlorine water and shampoos. L indicates how much the color has faded. The higher the L value, the lighter the color, i.e., the more fading has occurred. The effects of the LAN and additional ingredients such as the proteins are also apparent.

| MEAN L VALUES | | | | |
|---|---|---|---|---|
| | Control | After 1 week of shampooing/chlorine water treatment | Change in L | % change in L |
| water only | 24.61 | 28.09 | 3.48 | 14.14% |
| regimen of invention | 23.96 | 25.61 | 1.65 | 6.89% |
| regimen w/o LAN, proteins, amino acids, vitamin E, or sunscreens | 24.74 | 27.46 | 2.72 | 10.89% |

It is clear that the smallest change in L, i.e., the least fading, occurred when the LAN-containing regimen of the invention was used.

What is claimed is:

1. A composition comprising:
   at least one organic phospholipid capable of forming bilayers in aqueous solution;
   at least one amphoteric surfactant; and
   at least one nonionic surfactant present in an amount by weight equal to or greater than the amount of said at least one phospholipid,
   wherein said at least one phospholipid, said at least one amphoteric surfactant, and said at least one nonionic surfactant are present in a combined amount sufficient to allow lipophilic ingredients to be incorporated into an aqueous solution containing said composition.

2. A composition according to claim 1, wherein said composition further comprises water.

3. A composition according to claim 1, wherein said at least one organic phospholipid capable of forming bilayers in aqueous solution is lecithin.

4. A composition according to claim 1, wherein said at least one phospholipid, said at least one amphoteric surfactant, and said at least one nonionic surfactant are present, respectively, in a ratio ranging from 1:2:2 to 1:4:4 by weight.

5. A composition according to claim 1, wherein said at least one phospholipid, said at least one amphoteric surfactant, and said at least one nonionic surfactant are present in a ratio of at 1:3:2 by weight, respectively.

6. A composition according to claim 1, wherein said nonionic surfactant is formed from a $C_8$ to $C_{24}$ fatty alcohol, a $C_8$ to $C_{24}$ fatty acid, or a $C_8$ to $C_{24}$ glyceride.

7. A composition according to claim 1, wherein said nonionic surfactant has an HLB of at least 10.

8. A composition according to claim 1, wherein said amphoteric surfactant is selected from betaines, sultaines, hydroxysultaines, alkyl amphodiacetates, alkyl amphodipropionates, imidazolines, and salts thereof.

9. A composition according to claim 8, wherein said amphoteric surfactant is cocamphodipropionate or cocamidopropyl hydroxysultaine.

10. A composition according to claim 1, wherein said organic phospholipid is present in an amount of greater than 0 to about 5% by weight relative to the total weight of the composition.

11. A composition according to claim 10, wherein said organic phospholipid is present in an amount of about 5% by weight relative to the total weight of the composition.

12. A composition according to claim 1, wherein said nonionic surfactant is present in an amount of about 5% to about 20% by weight relative to the total weight of the composition.

13. A composition according to claim 1, wherein said amphoteric surfactant is present in an amount of about 5% to about 20% by weight relative to the total weight of the composition.

14. A composition according to claim 1, wherein the pH of said composition ranges from 4–12.

15. A composition according to claim 14, wherein said pH ranges from 10–12.

16. A delivery system for lipophilic materials comprising:
    an organic phospholipid capable of forming bilayers in aqueous solution;
    an amphoteric surfactant;
    a nonionic surfactant present in an amount by weight equal to or greater than the amount of said organic phospholipid;
    a lipophilic ingredient other than said phospholipid; and
    an aqueous phase, wherein said organic phospholipid, said nonionic surfactant, and said amphoteric surfactant are present in a combined amount sufficient to allow said lipophilic ingredient to be incorporated into said system, and
    wherein said system exhibits substantially no phase separation.

17. A system according to claim 16, wherein said aqueous phase further comprises additional ingredients selected from anionic surfactants, inorganic salts, proteins, hair dyes, water-soluble polymers, and amino acids.

18. A system according to claim 16, wherein said organic phospholipid is lecithin, said nonionic surfactant is selected from PPG-5-Ceteth-20 and Oleth-10, said amphoteric surfactant is disodium cocamphodipropionate, and said lipophilic ingredient is selected from olive oil, mineral oil, Vitamin E, octyl salicylate, octyl methoxycinnamate, silicones, and ceramides.

19. A system according to claim 16, wherein said system is in the form of a shampoo, a conditioner, a deep treatment for hair, a body wash, a bath gel, a bath oil, a hair dyeing composition, a permanent wave formulation, a make-up composition, a skin cream, or a lotion.

20. A process for the preparation of a delivery system as claimed in claim 16, said process comprising the following steps:
    (a) combining said organic phospholipid, said nonionic surfactant, and said amphoteric surfactant to obtain a mixture;
    (b) heating the mixture obtained in step (a);

(c) adding an aqueous solution to form a diluted mixture; and (d) cooling said diluted mixture.

21. The process of claim 20, wherein a lipophilic ingredient is added to the mixture of step (a).

22. The process of claim 21, wherein said lipophilic ingredient is a silicone, an oil-soluble vitamin, a ceramide, or a natural oil.

* * * * *

UNITED STATES PATENT AND TRADEMARK OFFICE
CERTIFICATE OF CORRECTION

PATENT NO. : 6,015,574
DATED : January 18, 2000
INVENTOR(S) : Cannell et al.

It is certified that error appears in the above-identified patent and that said Letters Patent is hereby corrected as shown below:

On the title page, Item [75] entitled "Inventors", line 2, "Hitren Mathur," should read -- Hiten Mathur--.

Signed and Sealed this

Twenty-third Day of January, 2001

Attest:

Q. TODD DICKINSON

*Attesting Officer*  *Commissioner of Patents and Trademarks*